(12) United States Patent
Lyons

(10) Patent No.: US 12,048,449 B2
(45) Date of Patent: Jul. 30, 2024

(54) ARTICULATING ULTRASONIC SURGICAL INSTRUMENTS AND SYSTEMS

(71) Applicant: Covidien LP, Mansfield, MA (US)

(72) Inventor: Michael B. Lyons, Boulder, CO (US)

(73) Assignee: Covidien LP, Mansfield, MA (US)

( * ) Notice: Subject to any disclaimer, the term of this patent is extended or adjusted under 35 U.S.C. 154(b) by 137 days.

(21) Appl. No.: 17/734,146

(22) Filed: May 2, 2022

(65) Prior Publication Data

US 2022/0249110 A1 Aug. 11, 2022

Related U.S. Application Data

(63) Continuation of application No. 16/557,123, filed on Aug. 30, 2019, now Pat. No. 11,337,717, which is a
(Continued)

(51) Int. Cl.
*A61B 17/295* (2006.01)
*A61B 17/29* (2006.01)
(Continued)

(52) U.S. Cl.
CPC ........ *A61B 17/295* (2013.01); *A61B 17/2909* (2013.01); *A61B 17/320092* (2013.01);
(Continued)

(58) Field of Classification Search
CPC .............. A61B 17/295; A61B 17/2909; A61B 17/32092; A61B 2017/2926;
(Continued)

(56) References Cited

U.S. PATENT DOCUMENTS

| 5,792,135 A | 8/1998 | Madhani et al. |
| 5,897,523 A | 4/1999 | Wright et al. |

(Continued)

FOREIGN PATENT DOCUMENTS

| EP | 2221011 A2 | 8/2010 |
| EP | 2807989 A1 | 12/2014 |

(Continued)

OTHER PUBLICATIONS

European search report issued in corresponding application No. 16199134.4 dated Jan. 18, 2017.
(Continued)

*Primary Examiner* — Tuan V Nguyen
(74) *Attorney, Agent, or Firm* — Carter, DeLuca & Farrell LLP

(57) ABSTRACT

An articulating ultrasonic surgical end effector includes a clevis, a transducer housing pivotably coupled to the clevis, an ultrasonic transducer disposed within the transducer housing, a waveguide extending distally from the ultrasonic transducer, an ultrasonic blade disposed at the distal end of the waveguide, a shaft extending distally from the transducer housing about at least a portion of the ultrasonic blade, and a clamp arm pivotably coupled to the shaft and movable relative to the ultrasonic blade between an open position and a clamping position. Ultrasonic energy produced by the ultrasonic transducer is transmitted along the waveguide to the ultrasonic blade for treating tissue therewith.

18 Claims, 4 Drawing Sheets

Related U.S. Application Data continuation of application No. 15/345,670, filed on Nov. 8, 2016, now Pat. No. 10,413,316.

(60) Provisional application No. 62/256,354, filed on Nov. 17, 2015.

(51) Int. Cl.
*A61B 17/32* (2006.01)
*A61B 34/30* (2016.01)

(52) U.S. Cl.
CPC ...... *A61B 34/30* (2016.02); *A61B 2017/2927* (2013.01); *A61B 2017/320075* (2017.08); *A61B 2017/320093* (2017.08); *A61B 2017/320094* (2017.08); *A61B 2017/320095* (2017.08); *A61B 2034/302* (2016.02); *A61B 2034/305* (2016.02)

(58) Field of Classification Search
CPC .... A61B 2017/2947; A61B 2017/2929; A61B 2017/2927; A61B 34/30
See application file for complete search history.

(56) References Cited

U.S. PATENT DOCUMENTS

| | | | |
|---|---|---|---|
| 6,394,998 B1 * | 5/2002 | Wallace | A61B 34/35 |
| | | | 901/29 |
| 6,491,701 B2 * | 12/2002 | Tierney | A61B 46/13 |
| | | | 606/130 |
| 7,135,030 B2 | 11/2006 | Schwemberger et al. | |
| 7,837,699 B2 * | 11/2010 | Yamada | A61B 17/320092 |
| | | | 600/459 |
| 10,413,316 B2 | 9/2019 | Lyons | |
| 11,337,717 B2 | 5/2022 | Lyons | |
| 2006/0058825 A1 | 3/2006 | Ogura et al. | |
| 2006/0190034 A1 | 8/2006 | Nishizawa et al. | |
| 2008/0214967 A1 | 9/2008 | Aranyi et al. | |
| 2009/0163948 A1 | 6/2009 | Sunaoshi et al. | |
| 2013/0012959 A1 | 1/2013 | Jinno | |
| 2013/0140835 A1 | 6/2013 | Stefanchik | |
| 2014/0005701 A1 | 1/2014 | Olson et al. | |
| 2014/0005702 A1 | 1/2014 | Timm et al. | |
| 2014/0276931 A1 | 9/2014 | Parihar et al. | |
| 2014/0309562 A1 | 10/2014 | Ito | |
| 2014/0350570 A1 | 11/2014 | Lee | |
| 2015/0080924 A1 | 3/2015 | Stulen et al. | |
| 2016/0302812 A1 | 10/2016 | Monroe et al. | |

FOREIGN PATENT DOCUMENTS

| | | | |
|---|---|---|---|
| JP | 2006075376 A | 3/2006 | |
| JP | 2011200593 A | 10/2011 | |
| JP | 2015501697 A | 1/2015 | |
| JP | 2015033090 A | 2/2015 | |
| JP | 2015528717 A | 10/2015 | |
| WO | 9952489 A1 | 10/1999 | |
| WO | 2014004112 A1 | 1/2014 | |
| WO | 2016003025 A1 | 1/2016 | |

OTHER PUBLICATIONS

Japanese office action issued in corresponding JP application No. 2016-223093 dated Sep. 8, 2017.

European Examination Report issued in corresponding EP application No. 16199134.4 dated Dec. 22, 2017, 6 pages.

* cited by examiner

ARTICULATING ULTRASONIC SURGICAL INSTRUMENTS AND SYSTEMS

CROSS REFERENCE TO RELATED APPLICATION

The present application is a continuation of U.S. patent application Ser. No. 16/557,123, filed on Aug. 30, 2019, which is a continuation of U.S. patent application Ser. No. 15/345,670, filed on Nov. 8, 2016 and now U.S. Pat. No. 10,413,316, which claims the benefit of and priority to U.S. Provisional Patent Application No. 62/256,354, filed on Nov. 17, 2015, the entire contents of each of which are hereby incorporated herein by reference.

BACKGROUND

Technical Field

The present disclosure relates to surgical instruments and systems and, more particularly, to articulating ultrasonic surgical instruments and systems.

Background of Related Art

Ultrasonic surgical instruments and systems utilize ultrasonic energy, i.e., ultrasonic vibrations, to treat tissue. More specifically, a typical ultrasonic surgical instrument or system includes a transducer configured to produce and transmit mechanical vibration energy at ultrasonic frequencies along a waveguide to an ultrasonic end effector configured to treat tissue, e.g., coagulate, cauterize, fuse, seal, cut, desiccate, fulgurate, or otherwise treat tissue. Traditionally, the transducer remains external of the surgical site, while the waveguide extends from the transducer into the surgical site to provide the ultrasonic energy to the ultrasonic end effector. The ultrasonic end effector is manipulated into position to treat a desired tissue or tissues.

Some ultrasonic surgical instruments and systems incorporate rotation features, thus enabling rotation of the ultrasonic end effector to a desired orientation within the surgical site. However, even in such instruments and systems, the ability to navigate within the surgical site via rotation and manipulation alone is limited.

SUMMARY

As used herein, the term "distal" refers to the portion that is being described which is further from a user, while the term "proximal" refers to the portion that is being described which is closer to a user. Further, to the extent consistent, any or all of the aspects detailed herein may be used in conjunction with any or all of the other aspects detailed herein.

In accordance with aspects of the present disclosure, an articulating ultrasonic surgical end effector is provided including a clevis, a transducer housing pivotably coupled to the clevis, an ultrasonic transducer disposed within the transducer housing, a waveguide extending distally from the ultrasonic transducer, an ultrasonic blade disposed at the distal end of the waveguide, a shaft extending distally from the transducer housing about at least a portion of the ultrasonic blade, and a clamp arm pivotably coupled to the shaft and movable relative to the ultrasonic blade between an open position and a clamping position. Ultrasonic energy produced by the ultrasonic transducer is transmitted along the waveguide to the ultrasonic blade for treating tissue therewith.

In aspects of the present disclosure, at least one pulley and cable operably couples the transducer housing with the clevis to permit pivoting of the transducer housing relative to the clevis.

In aspects of the present disclosure, at least one pulley and cable extends between the clamp arm and the clevis to permit pivoting of the clamp arm relative to the ultrasonic blade regardless of the orientation of the transducer housing relative to the clevis.

In aspects of the present disclosure, the transducer housing is pivotable relative to the clevis within a first plane and the clamp arm is pivotable relative to the ultrasonic blade within a second plane perpendicular to the first plane.

In aspects of the present disclosure, the transducer housing is pivotable relative to the clevis within a first plane and the clamp arm is pivotable relative to the ultrasonic blade within a second plane parallel to or co-planar with the first plane.

In aspects of the present disclosure, the ultrasonic transducer includes a plurality of piezoelectric elements and a plurality of electrodes interdisposed between the piezoelectric elements. The ultrasonic transducer, in aspects, defines a circular cross-sectional configuration. Alternatively, the ultrasonic transducer devices a rectangular cross-sectional configuration.

A surgical instrument provided in accordance with aspects of the present disclosure includes a handle assembly having an elongated body portion extending distally therefrom, and an articulating ultrasonic surgical end effector according to any of the above aspects, wherein the clevis thereof extends distally from the elongated body portion of the handle assembly.

A surgical system provided in accordance with aspects of the present disclosure includes a robotic surgical system having a control device and a robotic arm, and an articulating ultrasonic surgical end effector according to any of the above aspects, wherein the clevis extends distally from the robotic arm of the robotic surgical system.

BRIEF DESCRIPTION OF THE DRAWINGS

The above and other aspects and features of the present disclosure will become more apparent in view of the following detailed description when taken in conjunction with the accompanying drawings wherein like reference numerals identify similar or identical elements and.

DETAILED DESCRIPTION

Figure 1:
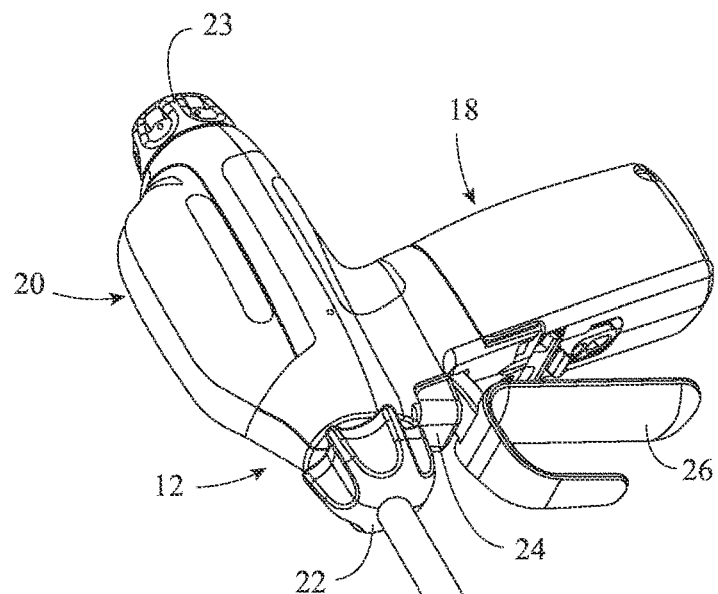
FIG. 1 is a side, perspective view of an endoscopic surgical instrument configured for use in accordance with the aspects and features of present disclosure.
Figure 1:
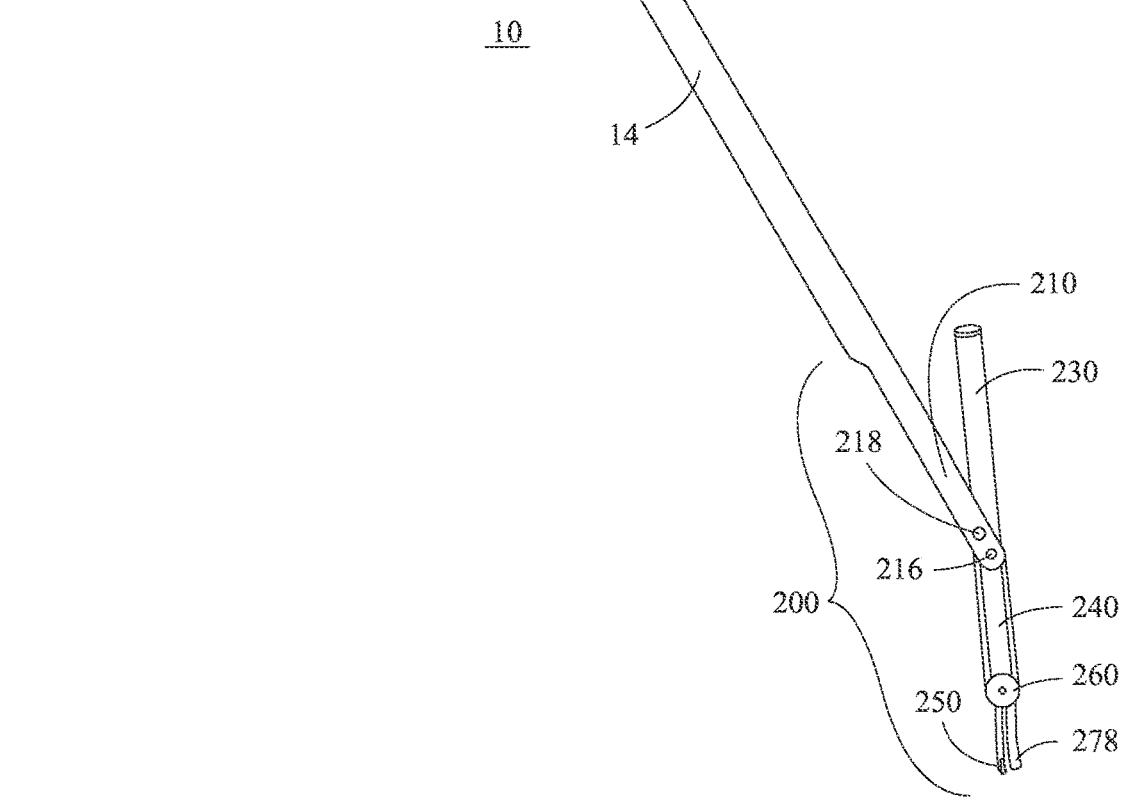

Referring generally to FIG. 1, an embodiment of an endoscopic surgical instrument exemplifying the aspects and features of the present disclosure is shown generally identified by reference numeral 10. For the purposes herein, endoscopic surgical instrument 10 is generally described. Aspects and features of endoscopic surgical instrument 10 not germane to the understanding of the present disclosure are omitted to avoid obscuring the aspects and features of the present disclosure in unnecessary detail.

Endoscopic surgical instrument 10 generally includes a handle assembly 12, an elongated body portion 14, and an articulating ultrasonic surgical end effector 200. End effector 200 is described in greater detail below. Handle assembly 12 supports a battery assembly 18 and a generator assembly 20, and includes a first rotation knob 22, a second rotation knob 23, an activation button 24, and a clamp trigger 26.

Clamp trigger 26 of endoscopic surgical instrument 10 is selectively manipulatable to actuate a motor, other powered drive mechanism, or a manual drive mechanism, e.g., gears, pulleys, tension cables, etc., to transition end effector 200 between an open condition and a clamping condition, as detailed below.

First rotation knob 22 is selectively manipulatable to rotate elongated body portion 14 and, thus, end effector 200 relative to handle assembly 12. Second rotation knob 23 is selectively manipulatable to actuate a motor, other powered drive mechanism, or a manual drive mechanism, e.g., gears, pulleys, tension cables, etc., to articulate end effector 200 relative to elongated body portion 12, as detailed below. As an alternative to first and second rotation knobs 22, 23, other suitable actuation mechanism, e.g., toggle switches, joysticks, buttons, etc., may be provided.

Battery assembly 18 and generator assembly 20 cooperate, upon activation of activation button 24, to supply power to end effector 200 to enable the generation of ultrasonic energy for treating tissue therewith, e.g., to coagulate, cauterize, fuse, seal, cut, desiccate, fulgurate, or otherwise treat tissue, as detailed below. Battery assembly 18 and generator assembly 20 are each releasably secured to handle assembly 12, and are removable therefrom to facilitate disposal of handle assembly 12, with the exception of battery assembly 18 and generator 20. However, it is contemplated that any or all of the components of endoscopic surgical instrument 10 be configured as disposable single-use components or sterilizable multi-use components, and/or that endoscopic surgical instrument 10 be connectable to a remote power source or generator rather than having such components on-board.

Figure 2:
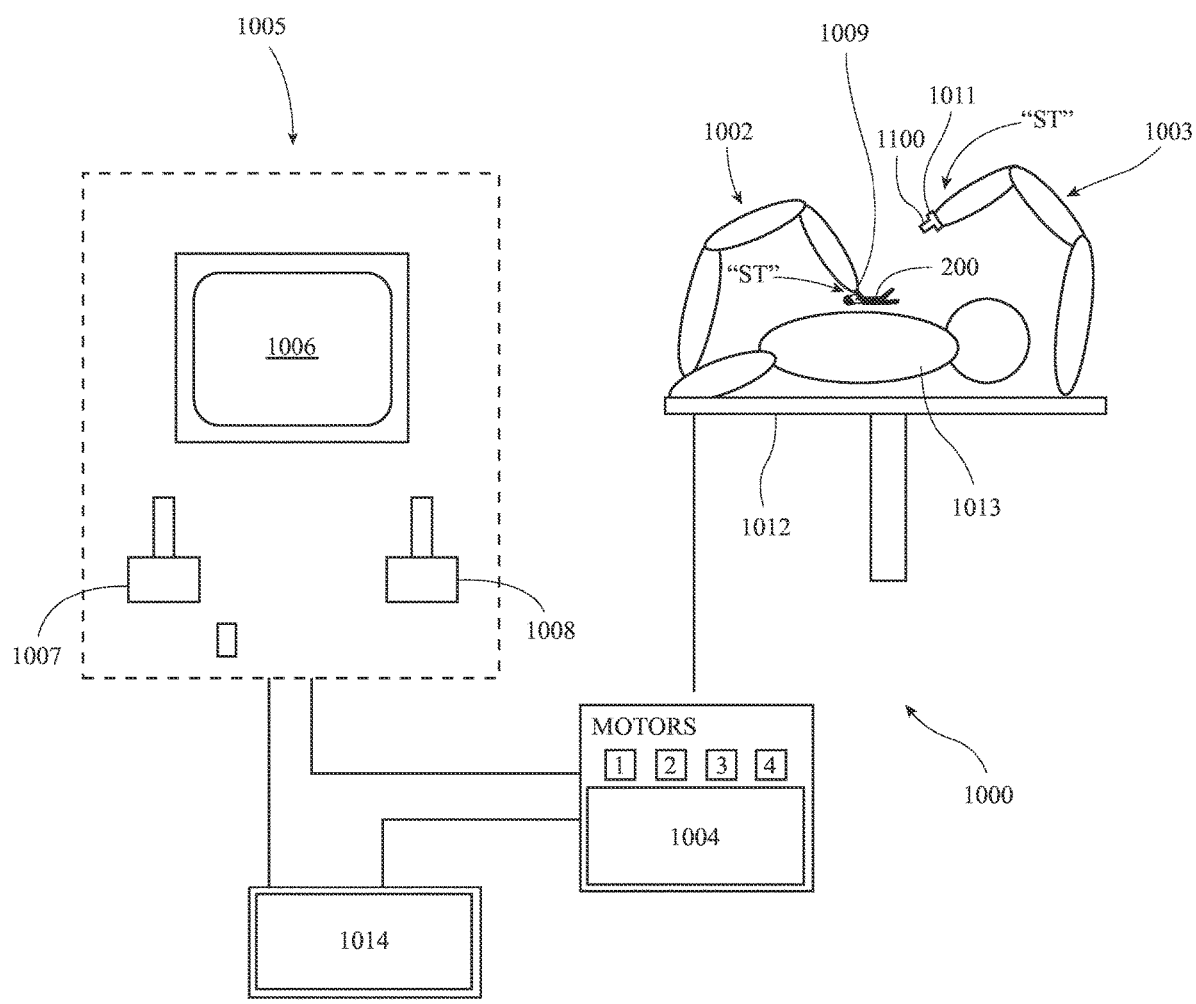
FIG. 2 is a schematic illustration of a robotic surgical system configured for use in accordance with the aspects and features of present disclosure.

Referring generally to FIG. 2, an embodiment of a robotic surgical system exemplifying the aspects and features of the present disclosure is shown generally identified by reference numeral 1000. For the purposes herein, robotic surgical system 1000 is generally described. Aspects and features of robotic surgical system 1000 not germane to the understanding of the present disclosure are omitted to avoid obscuring the aspects and features of the present disclosure in unnecessary detail.

Robotic surgical system 1000 generally includes a plurality of robot arms 1002, 1003; a control device 1004; and an operating console 1005 coupled with control device 1004. Operating console 1005 may include a display device 1006, which may be set up in particular to display three-dimensional images; and manual input devices 1007, 1008, by means of which a person (not shown), for example a surgeon, may be able to telemanipulate robot arms 1002, 1003 in a first operating mode. Robotic surgical system 1000 may be configured for use on a patient 1013 lying on a patient table 1012 to be treated in a minimally invasive manner. Robotic surgical system 1000 may further include a database 1014, in particular coupled to control device 1004, in which are stored, for example, pre-operative data from patient 1013 and/or anatomical atlases.

Each of the robot arms 1002, 1003 may include a plurality of members, which are connected through joints, and an attaching device 1009, 1011, to which may be attached, for example, a surgical tool "ST" supporting an end effector 200, 1100. End effector 200, as noted above with respect to endoscopic surgical instrument 10 (FIG. 1), and as described in greater detail below, is an articulating ultrasonic surgical end effector. End effector 1100 may be any other suitable surgical end effector, e.g., an endoscopic camera, other surgical tool, etc. Robot arms 1002, 1003 may be driven by electric drives, e.g., motors, that are connected to control device 1004. Control device 1004 (e.g., a computer) may be configured to activate the motors, in particular by means of a computer program, in such a way that robot arms 1002, 1003, their attaching devices 1009, 1011, and, thus, the surgical tools "ST" (including end effectors 200, 1100) execute a desired movement and/or function according to a corresponding input from manual input devices 1007, 1008, respectively. Control device 1004 may also be configured in such a way that it regulates the movement of robot arms 1002, 1003 and/or of the motors.

Figure 3A:
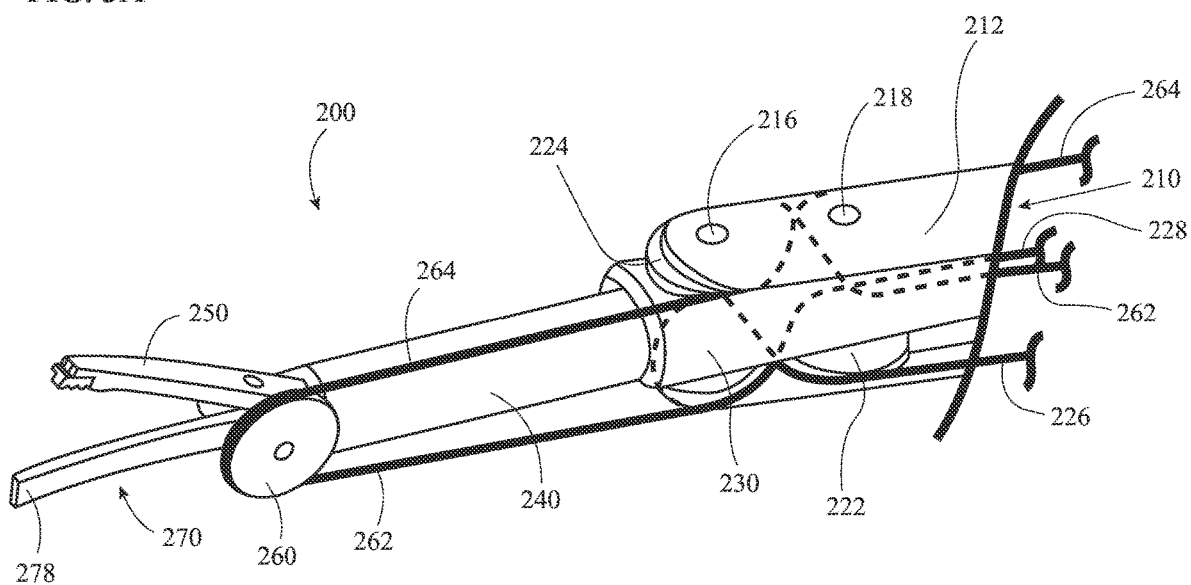
FIG. 3A is an enlarged, side, perspective view of an ultrasonic articulating end effector in accordance with the present disclosure and configured for use with the endoscopic surgical instrument of FIG. 1, the robotic surgical system of FIG. 2, or any other suitable surgical instrument or system.

Turning to FIG. 3A, articulating ultrasonic surgical end effector 200 includes a clevis 210 that operably couples end effector 200 to a surgical instrument or system. For example, clevis 210 may be defined at the distal end of elongated body portion 14 of endoscopic surgical instrument 10 (FIG. 1), at the distal end of attaching device 1009 of robot arm 1002 of robotic surgical system 1000 (FIG. 2), or at any other suitable location for enabling use of end effector 200 with a corresponding surgical instrument or system.

Clevis 210 includes a pair of spaced-apart arms 212. Each arm 212 defines a distal aperture 216 and a proximal aperture 218. Distal apertures 216 are aligned with one another and proximal apertures 218 are aligned with one another. A proximal pulley 222 is disposed adjacent each proximal aperture 218 on the interior sides of arms 212. Proximal pulleys 222 are rotatably coupled to adjacent arms 212 via pivot pins (not explicitly shown) extending through proximal apertures 218.

Continuing with reference to FIG. 3A, end effector assembly 200 further includes a transducer housing 230, a shaft 240 extending distally from transducer housing 230, a clamp arm 250 pivotable relative to shaft 240, a clamp pulley 260 operably coupled to clamp arm 250, and an inner assembly 270 disposed partially within transducer housing 230, extending through shaft 240, and extending distally from shaft 240. Transducer housing 230 mounts a distal pulley 224 on either side thereof. Transducer housing 230 extends between arms 212 of clevis 210 such that one of distal pulleys 224 is disposed adjacent each distal apertures 216 on the interior sides of arms 212. Distal pulleys 224 are rotatably coupled to arms 212 via pivot pins (not explicitly shown) extending through distal apertures 216.

Referring still to FIG. 3A, first and second cables 226, 228 are each routed about one of the proximal pulleys 222 and are secured to one of the distal pulleys 224. More specifically, a distal end of first cable 226 is routed about the corresponding distal pulley 224 in a first direction and is secured thereto, while a distal end of second cable 228 is routed about the corresponding distal pulley 224 and is secured thereto. As a result of this configuration, proximal pulling of first cable 226 urges the corresponding distal pulley 224 and, thus, transducer housing 230 to pivot relative to clevis 210 in a first direction, while proximal pulling of second cable 228 urges the corresponding distal pulley 224 and, thus, transducer housing 230 to pivot relative to clevis 210 in a second, opposite direction. Alternatively, first and second cables 226, 228 may be configured as a single cable secured to one of the distal pulleys 224, routed about one of the proximal pulleys 222, and having its two ends extending proximally from clevis 210.

Shaft 240 of end effector 200 extends distally from transducer housing 230 and includes clamp arm 250 pivotably coupled thereto. Clamp pulley 260 is engaged with clamp arm 250 and rotatably coupled to the distal end of shaft 240 such that rotation of clamp pulley 260 in a first direction relative to shaft 240 pivots clamp arm 250 towards a clamping position, wherein clamp arm 250 is positioned adjacent ultrasonic blade 278 for clamping tissue therebetween, and such that rotation of clamp pulley 260 in a second, opposite direction relative to shaft 240 pivots clamp arm 250 towards an open positon, wherein clamp arm 250 is further-spaced from ultrasonic blade 278.

Third and fourth cables 262, 264 are routed about proximal pulleys 222, distal pulleys 224, and clamp pulley 260. More specifically, a distal end of third cable 262 is routed about clamp pulley 260 in a first direction and is secured thereto, while a distal end of fourth cable 264 is routed about clamp pulley 260 in a second direction and is secured thereto. As a result of this configuration, proximal pulling of third cable 262 urges clamp pulley 260 to pivot relative to shaft 240 in a first direction, thereby pivoting clamp arm 250 relative to ultrasonic blade 278 towards the clamping position, while proximal pulling of fourth cable 264 urges clamp pulley 260 to pivot relative to shaft 240 in a second, opposite direction, thereby pivoting clamp arm 250 relative to ultrasonic blade 278 towards the open position. Alternatively, third and fourth cables 262, 264 may be configured as a single cable secured about clamp pulley 260 and having its two ends extending proximally from clamp pulley 260, about proximal and distal pulleys 222, 224, and proximally from clevis 210.

Referring additionally to FIG. 1, with respect to use of end effector 200 with endoscopic surgical instrument 10, the proximal ends of first, second, third, and fourth cables 226, 228, 262, 264 of end effector 200 extend proximally through elongated body portion 12. The proximal ends of first and second cables 226, 228 are operably coupled to second rotation knob 23 (or the drive component associated therewith) such that rotation of second rotation knob 23 in a first direction pivots transducer housing 230 relative to clevis 210 and elongated body portion 12 in a first direction, and such that rotation of second rotation knob 23 in a second direction pivots transducer housing 230 relative to clevis 210 and elongated body portion 12 in a second direction. Such a configuration enables articulation of clamp arm 250 and ultrasonic blade 278 to a desired orientation relative to tissue to be treated.

The proximal ends of third and fourth cables 262, 264 are operably coupled to clamp trigger 26 such that actuation of clamp trigger 26 from an un-actuated position to an actuated position pivots clamping arm 260 from the open position to the clamping position and such that return of clamp trigger 26 from the actuated position back to the un-actuated position pivots clamping arm 260 from the clamping position back to the open position.

Referring to FIGS. 2 and 3A, with respect to use of end effector 200 with robotic surgical system 1000, the proximal ends of first, second, third, and fourth cables 226, 228, 262, 264 of end effector 200 extend proximally through robot arm 1002 and each operably couple to a corresponding motor of control device 1004. Control device 1004 is operable, depending upon the input instructions received, to drive the appropriate motor thereof to pull the corresponding cable 226, 228, 262, 264 to pivot transducer housing 230 relative to clevis 210 in a desired direction to articulate clamp arm 250 and ultrasonic blade 278 to a desired orientation relative to tissue to be treated, or to pivot clamp arm 250 between the open and clamping positions to clamp tissue between clamp arm 250 and ultrasonic blade 278.

Figure 3B:
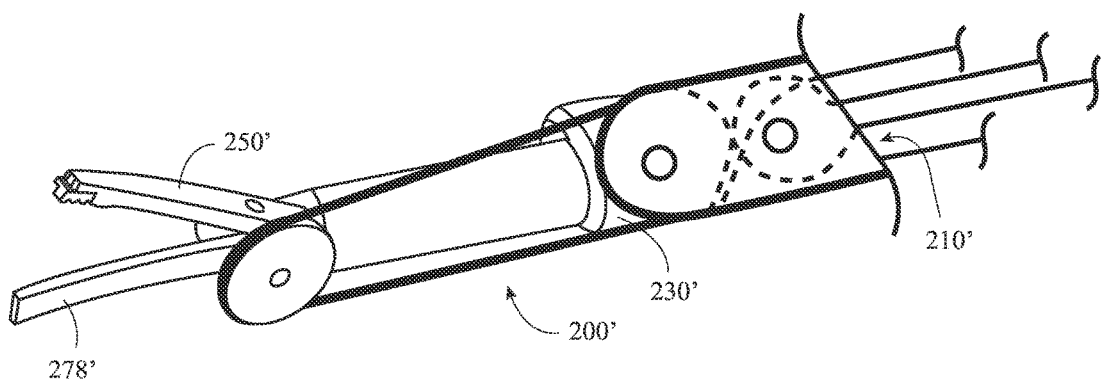
FIG. 3B is an enlarged, side, perspective view of another ultrasonic articulating end effector in accordance with the present disclosure and configured for use with the endoscopic surgical instrument of FIG. 1, the robotic surgical system of FIG. 2, or any other suitable surgical instrument or system.

In the configuration illustrated in FIG. 3A, clamp arm 250 pivots between the open and clamping positions within a first plane and transducer housing 230 pivots or articulates relative to clevis 210 within a second plane that is perpendicular to the first plane. Alternatively, as illustrated in FIG. 3B, an end effector 200' similar to end effector 200 (FIG. 3A) may be provided wherein clamp arm 250' pivots relative to ultrasonic blade 278' within a first plane and transducer housing 230' pivots relative to clevis 210' within a second plane that is parallel or co-planar with the first plane.

Figure 4:
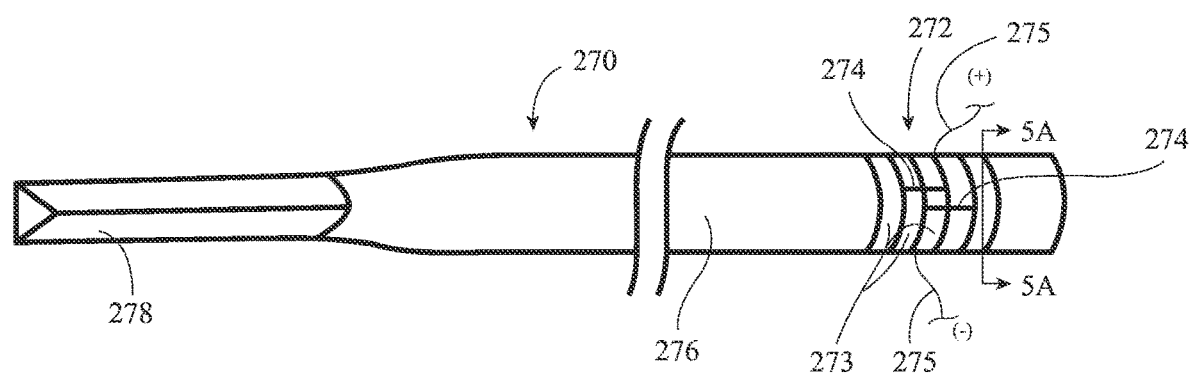
FIG. 4 is a side view of the transducer, waveguide, and ultrasonic blade of the ultrasonic articulating end effector of FIG. 3A.

Referring to FIGS. 3A and 4, as noted above, inner assembly 270 is disposed partially within transducer housing 230, extends through shaft 240, and extends distally from shaft 240. Inner assembly 270 includes an ultrasonic transducer 272 formed from a stack of piezoelectric elements 273. Electrodes 274 interdisposed between piezoelectric elements 273 are electrically coupled to a source of energy, e.g., via lead wires 275 extending through the pivots that couple transducer housing 230 with clevis 210 and proximally through the instrument or system to the source of energy. Upon energization of electrodes 274, e.g., in response to activation of activation button 26 of surgical instrument (FIG. 1) or in response to an appropriate instruction provided by control device 1004 of robotic surgical system 1000 (FIG. 2), piezoelectric elements 273 produce ultrasonic energy that is transmitted along waveguide 276, which extends from ultrasonic transducer 272 distally from transducer housing 230 and through shaft 240. Ultrasonic blade 278 extends distally from waveguide 276 and distally from shaft 240. Ultrasonic blade 278 is positioned adjacent clamp arm 250 to enable clamping of tissue between ultrasonic blade 278 and clamp arm 250 in the clamping position of clamp arm 250. Ultrasonic energy transmitted along waveguide 276 to ultrasonic blade 278 is communicated to tissue clamped between clamp arm 250 and ultrasonic blade 278 to treat tissue.

Figure 5A:
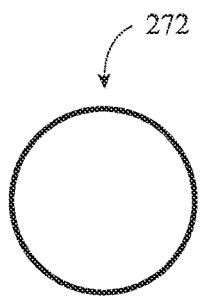
FIG. 5A is a cross-sectional view of the transducer of the ultrasonic articulating end effector of FIG. 3A taken across section line 5A-5A of FIG. 4.
Figure 5B:
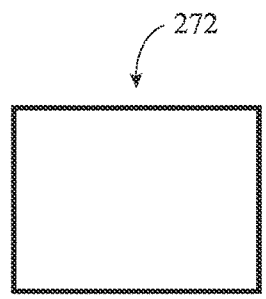
FIG. 5B is a cross-sectional view of another transducer configured for use with the ultrasonic articulating end effector of FIG. 3A.

Turning now to FIG. 5A, in some embodiments, piezoelectric elements 273 of ultrasonic transducer 272 define a generally circular cross-sectional configuration. Alternatively, as illustrated in FIG. 5B, piezoelectric elements 273 of ultrasonic transducer 272 may define a rectangular cross-sectional configuration. The rectangular configuration illustrated in FIG. 5B provides a greater surface area usable to create ultrasonic energy without requiring an increase in the required dimensions of end effector 200.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An ultrasonic surgical instrument, comprising:
    an elongated body; and
    an end effector assembly, the end effector assembly including:
        a transducer housing articulatably coupled to a distal end portion of the elongated body to permit articulation of the transducer housing relative to the elongated body;
        an ultrasonic transducer disposed at least partially within the transducer housing;
        an ultrasonic blade coupled to and extending distally from the ultrasonic transducer, wherein ultrasonic energy produced by the ultrasonic transducer is transmitted to the ultrasonic blade to treat tissue in contact with eh ultrasonic blade; and
        a clamp arm pivotable relative to the ultrasonic blade about a clamp arm pivot between an open position and a clamping position, wherein the ultrasonic transducer, the ultrasonic blade, and the clamp arm are configured to articulate together with the transducer housing when the transducer housing is articulated relative to the elongated body, and wherein the ultrasonic blade is disposed in fixed orientation relative to the clamp arm pivot;
    first and second cable sections routed through the elongated body to the transducer housing, the first cable section coupled to the transducer housing such that proximal pulling of the first cable section articulates the transducer housing relative to the elongated body in a first direction and the second cable section coupled to the transducer housing such that proximal pulling of the second cable section articulates the transducer housing relative to the elongated body in a second, opposite direction; and
    third and fourth cable sections routed through the elongated body to the clamp arm, the third cable section coupled to the clamp arm such that proximal pulling of the third cable section pivots the clamp arm towards the clamping position and the fourth cable section coupled to the clamp arm such that proximal pulling of the fourth cable section pivots the clamp arm towards the open position.

2. The ultrasonic surgical instrument according to claim 1, wherein the transducer housing is articulatably coupled to a clevis disposed at the distal end portion of the elongated body.

3. The ultrasonic surgical instrument according to claim 1, wherein the first and second cable sections are coupled to the transducer housing via a first pulley arrangement.

4. The ultrasonic surgical instrument according to claim 1, wherein the third cable section is coupled to a clamp pulley engaged to the clamp arm.

5. The ultrasonic surgical instrument according to claim 1, wherein the fourth cable section is coupled to a clamp pulley engaged to the clamp arm.

6. The ultrasonic surgical instrument according to claim 1, wherein the third and fourth cable sections are coupled to the clamp arm via a second pulley arrangement.

7. The ultrasonic surgical instrument according to claim 1, wherein the end effector assembly further includes a shaft extending distally from the transducer housing, wherein the clamp arm is pivotably coupled to the shaft.

8. The ultrasonic surgical instrument according to claim 1, further comprising an ultrasonic waveguide coupling the ultrasonic transducer and the ultrasonic blade with one another.

9. The ultrasonic surgical instrument according to claim 1, wherein the first, second, third, and fourth cable sections are configured to operably couple to corresponding motors of a robotic surgical system.

10. The ultrasonic surgical instrument according to claim 1, wherein the transducer housing is pivotably coupled to the distal end portion of the elongated body about a pivot axis to permit articulation of the transducer housing relative to the elongated body about the pivot axis.

11. An ultrasonic surgical system, comprising:
    a robotic surgical system including a control device and a plurality of motors; and
    an ultrasonic surgical instrument configured to releasably couple to the robotic surgical system, the ultrasonic surgical instrument including:
        an elongated body; and
        an end effector assembly articulatably coupled to a distal end portion of the elongated body to permit articulation of the end effector assembly relative to the elongated body, the end effector assembly including:
            an ultrasonic transducer;
            an ultrasonic blade coupled to and extending distally from the ultrasonic transducer; and
            a clamp arm pivotable relative to the ultrasonic blade about a clamp arm pivot between an open position and a clamping position, wherein the ultrasonic blade is disposed in fixed orientation relative to the clamp arm pivot;
        first and second cable sections operably coupled to corresponding motors of the plurality of motors and routed through the elongated body to the end effector assembly, the first cable section coupled to the end effector assembly such that proximal pulling of the first cable section articulates the end effector assembly relative to the elongated body in a first direction and the second cable section coupled to the end effector assembly such that proximal pulling of the second cable section articulates the end effector assembly relative to the elongated body in a second, opposite direction; and
        third and fourth cable sections operably coupled to corresponding motors of the plurality of motors and routed through the elongated body to the clamp arm, the third cable section coupled to the clamp arm such that proximal pulling of the third cable section pivots the clamp arm towards the clamping position and the fourth cable section coupled to the clamp arm such that proximal pulling of the fourth cable section pivots the clamp arm towards the open position.

12. The ultrasonic surgical system according to claim 11, further comprising a transducer housing at least partially retaining the ultrasonic transducer therein, the transducer housing articulatably coupled to the distal end portion of the elongated body.

13. The ultrasonic surgical system according to claim 12, wherein the transducer housing is articulatably coupled to the distal end portion of the elongated body via a clevis.

14. The ultrasonic surgical system according to claim 11, wherein the first and second cable sections are coupled to the end effector assembly via a first pulley arrangement.

15. The ultrasonic surgical system according to claim 11, wherein the third cable section is coupled to a clamp pulley engaged to the clamp arm.

16. The ultrasonic surgical system according to claim 11, wherein the fourth cable section is coupled to a clamp pulley engaged to the clamp arm.

17. The ultrasonic surgical system according to claim 11, wherein the third and fourth cable sections are coupled to the clamp arm via a second pulley arrangement.

18. The ultrasonic surgical system according to claim 11, further comprising an ultrasonic waveguide coupling the ultrasonic transducer and the ultrasonic blade with one another.

\* \* \* \* \*